US012642550B2

(12) United States Patent
Anderson et al.

(10) Patent No.: US 12,642,550 B2
(45) Date of Patent: Jun. 2, 2026

(54) METHOD AND APPARATUS FOR TISSUE GRAFTING

(71) Applicant: The General Hospital Corporation, Boston, MA (US)

(72) Inventors: Richard Rox Anderson, Boston, MA (US); William A. Farinelli, Danvers, MA (US); Michael R. Hamblin, Revere, MA (US); Dieter Manstein, Coral Gables, FL (US)

(73) Assignee: The General Hospital Corporation, Boston, MA (US)

( * ) Notice: Subject to any disclaimer, the term of this patent is extended or adjusted under 35 U.S.C. 154(b) by 919 days.

(21) Appl. No.: 16/922,990

(22) Filed: Jul. 7, 2020

(65) Prior Publication Data

US 2020/0360043 A1    Nov. 19, 2020

Related U.S. Application Data

(63) Continuation of application No. 15/785,897, filed on Oct. 17, 2017, now Pat. No. 10,716,591, which is a
(Continued)

(51) Int. Cl.
A61B 17/3205 (2006.01)
A61B 17/32 (2006.01)
(Continued)

(52) U.S. Cl.
CPC .................. A61B 17/32053 (2013.01); A61B 17/320068 (2013.01); A61B 17/322 (2013.01);
(Continued)

(58) Field of Classification Search
CPC ...... A61B 17/32053; A61B 17/320068; A61B 17/322; A61B 17/32093; A61B 10/0233;
(Continued)

(56) References Cited

U.S. PATENT DOCUMENTS

| 2,426,535 | A | 8/1947 | Turkel |
| 3,598,108 | A | 8/1971 | Jamshidi et al. |

(Continued)

FOREIGN PATENT DOCUMENTS

| CN | 2126570 | Y | 1/1993 |
| CN | 1115629 | A | 1/1996 |

(Continued)

OTHER PUBLICATIONS

Alsberg et al., Engineering Growing Tissues, PNAS, 2002, 99(19): 12025-12030.

(Continued)

*Primary Examiner* — Anh T Dang
(74) *Attorney, Agent, or Firm* — QUARLES & BRADY LLP

(57) ABSTRACT

Exemplary embodiments of apparatus and method for harvesting small portions of tissue ("micrografts") to form grafts can be provided. For example, a hollow tube can be inserted into tissue at a donor site, where a distal end of the hollow tube can have two or more points or extensions to facilitate separation of the micrografts from the surrounding tissue. The exemplary apparatus can be provided that includes a plurality of such tubes for simultaneous harvesting of a plurality of micrografts. The harvested micrografts can have a small dimension, e.g., less than about 1 mm, or less than about 0.3 mm, which can promote healing of the donor site and/or viability of the harvested tissue. The micrografts can be approximately cylindrical or strip-shaped, and can be placed in a biocompatible matrix to form a graft or directly into tissue at the recipient site. Such exemplary micrografts can be obtained from skin or other types of tissue, e.g., various internal organs.

20 Claims, 5 Drawing Sheets

Related U.S. Application Data continuation of application No. 12/936,173, filed as application No. PCT/US2009/039114 on Apr. 1, 2009, now Pat. No. 9,827,006.

(60) Provisional application No. 61/041,587, filed on Apr. 1, 2008.

(51) Int. Cl.
| | |
|---|---|
| *A61B 17/322* | (2006.01) |
| *A61B 10/02* | (2006.01) |
| *A61B 17/00* | (2006.01) |
| *A61B 17/30* | (2006.01) |
| *A61B 17/3209* | (2006.01) |

(52) U.S. Cl.
CPC . *A61B 10/0233* (2013.01); *A61B 2017/00752* (2013.01); *A61B 2017/00969* (2013.01); *A61B 2017/306* (2013.01); *A61B 17/32093* (2013.01); *A61B 2017/3225* (2013.01)

(58) Field of Classification Search
CPC ........... A61B 2017/00752; A61B 2017/00969; A61B 2017/603; A61B 2017/3225
See application file for complete search history.

(56) References Cited

U.S. PATENT DOCUMENTS

| | | | |
|---|---|---|---|
| 3,608,553 A * | 9/1971 | Balamuth ............ A61B 17/322 | |
| | | | 601/2 |
| 3,788,320 A | 1/1974 | Dye | |
| 3,867,942 A * | 2/1975 | Bellantoni ................ A61F 2/10 | |
| | | | 408/129 |
| 4,403,617 A | 9/1983 | Tretinyak | |
| 4,458,678 A | 7/1984 | Yannas et al. | |
| 4,476,864 A * | 10/1984 | Tezel ............... A61B 17/32053 | |
| | | | 600/568 |
| 4,604,346 A | 8/1986 | Bell et al. | |
| 4,640,296 A | 2/1987 | Schnepp-Pesch et al. | |
| 4,832,045 A | 5/1989 | Goldberger | |
| 5,152,763 A | 10/1992 | Johnson | |
| 5,331,972 A | 7/1994 | Wadhwani et al. | |
| 5,415,182 A | 5/1995 | Chin et al. | |
| 5,439,475 A | 8/1995 | Bennett | |
| 5,611,810 A | 3/1997 | Arnold et al. | |
| 5,639,654 A | 6/1997 | Bernard et al. | |
| 5,782,843 A | 7/1998 | Aasberg | |
| 5,792,169 A | 8/1998 | Markman | |
| 5,827,297 A | 10/1998 | Boudjema | |
| 5,885,226 A | 3/1999 | Rubinstein et al. | |
| 5,922,000 A | 7/1999 | Chodorow | |
| 5,928,162 A | 7/1999 | Giurtino et al. | |
| 6,059,807 A | 5/2000 | Boudjema | |
| 6,110,189 A | 8/2000 | Markman | |
| 6,440,086 B1 | 8/2002 | Hohenberg | |
| 6,997,923 B2 | 2/2006 | Anderson et al. | |
| 7,073,510 B2 | 7/2006 | Redmond et al. | |
| 9,060,803 B2 | 6/2015 | Anderson et al. | |

| | | |
|---|---|---|
| 2002/0055689 A1 | 5/2002 | Kaplan et al. |
| 2002/0103500 A1 | 8/2002 | Gildenberg |
| 2003/0195625 A1 | 10/2003 | Garcia Castro et al. |
| 2004/0002723 A1 | 1/2004 | Ball |
| 2004/0054410 A1 | 3/2004 | Barrows |
| 2005/0171567 A1 | 8/2005 | Dehart |
| 2005/0226856 A1 | 10/2005 | Ahlfors |
| 2005/0267506 A1 | 12/2005 | Harris |
| 2006/0155266 A1 | 7/2006 | Manstein et al. |
| 2006/0161179 A1 * | 7/2006 | Kachenmeister ........................... A61B 17/32053 606/133 |
| 2006/0216781 A1 | 9/2006 | Gebing |
| 2007/0031092 A1 | 2/2007 | Saitoh et al. |
| 2007/0038236 A1 | 2/2007 | Cohen |
| 2007/0073327 A1 * | 3/2007 | Giovannoli ...... A61B 17/32093 606/186 |
| 2007/0106306 A1 | 5/2007 | Bodduluri et al. |
| 2007/0142722 A1 | 6/2007 | Chang |
| 2007/0142744 A1 | 6/2007 | Provencher |
| 2007/0156164 A1 * | 7/2007 | Cole .................. A61B 17/3468 606/187 |
| 2007/0270710 A1 | 11/2007 | Frass et al. |
| 2008/0039685 A1 | 2/2008 | Komiya et al. |
| 2008/0045861 A1 | 2/2008 | Miller et al. |
| 2008/0051805 A1 | 2/2008 | Pinchuk |
| 2009/0146068 A1 | 6/2009 | Agarwal |
| 2009/0198336 A1 | 8/2009 | Qiao et al. |
| 2010/0041938 A1 | 2/2010 | Stoianovici et al. |
| 2012/0041430 A1 | 2/2012 | Anderson et al. |

FOREIGN PATENT DOCUMENTS

| | | |
|---|---|---|
| DE | 287651 A5 | 3/1991 |
| DE | 9211681 U1 | 11/1992 |
| JP | S57163208 U | 10/1982 |
| JP | H07100140 A | 4/1995 |
| JP | H10210 A | 1/1998 |
| JP | 2000139929 A | 5/2000 |
| JP | 2005137454 A | 6/2005 |
| JP | 2007229330 A | 9/2007 |
| WO | 199200706 A1 | 1/1992 |
| WO | 9921497 A1 | 5/1999 |
| WO | 0064379 A1 | 11/2000 |
| WO | 2000074763 A2 | 12/2000 |
| WO | 02096321 A1 | 12/2002 |
| WO | 2005072181 A2 | 8/2005 |
| WO | 2005109799 A2 | 11/2005 |
| WO | 2007041267 A2 | 4/2007 |

OTHER PUBLICATIONS

Moore et al., Modeling of the Plane Needle Cutting Edge Rake and Inclination Angles for Biopsy, Journal of Manufacturing Science and Engineering, 2010, 132:051005-1 thru 051005-8.

PCT International Search Report and Written Opinion, PCT/US2009/039114, Nov. 16, 2009, 10 pages.

Extended European Search Report in European Application No. 25154521.6.

* cited by examiner

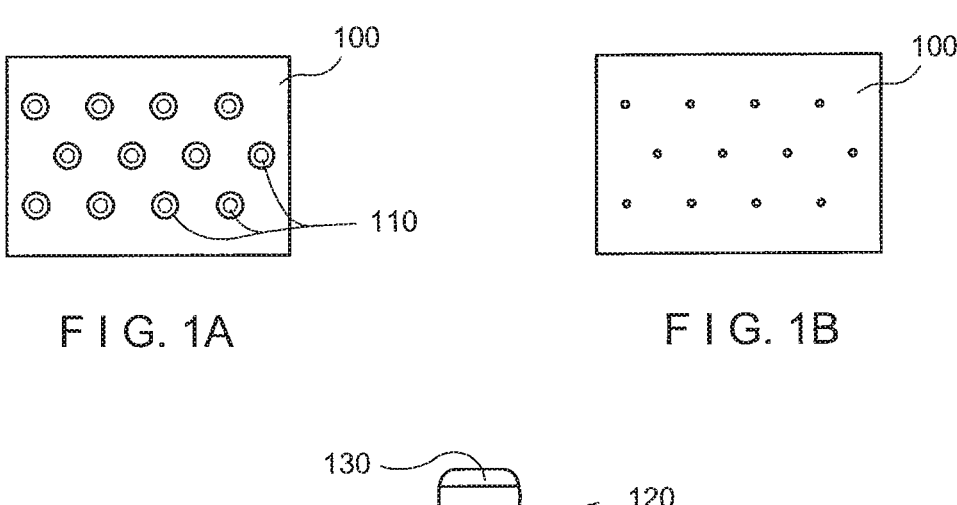
F I G. 1A                    F I G. 1B
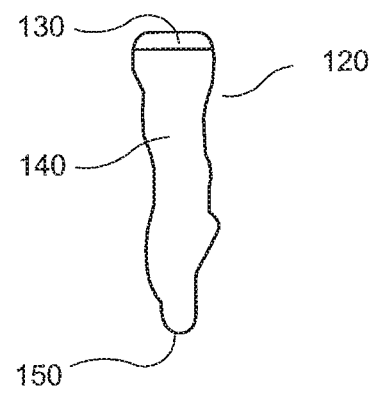
F I G. 1C
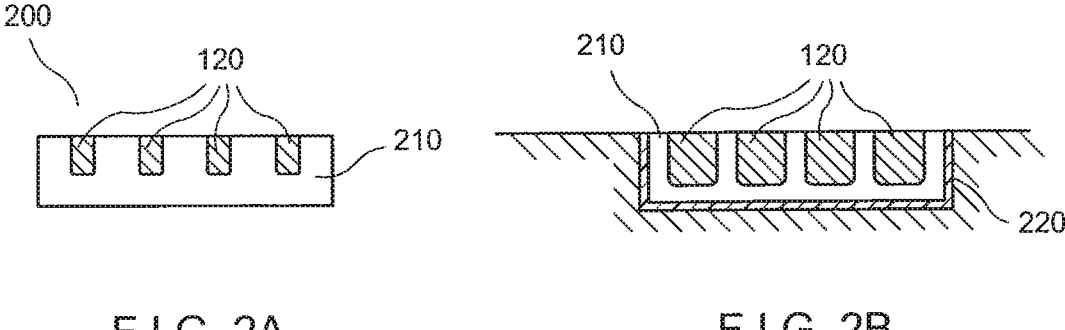
F I G. 2A                    F I G. 2B

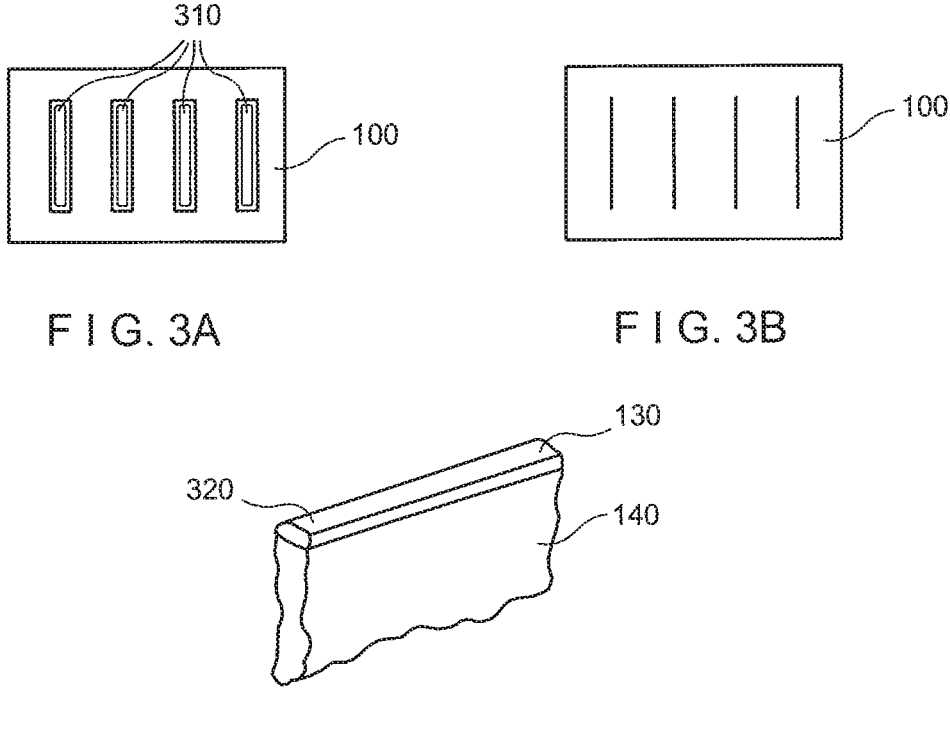
FIG. 3A                                    FIG. 3B
FIG. 3C
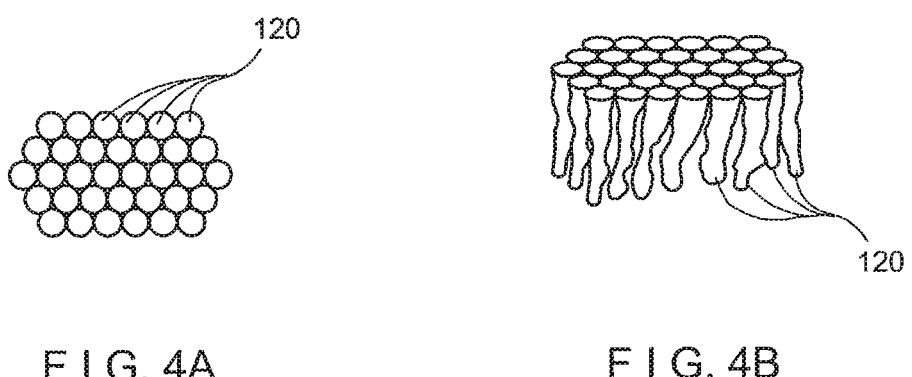
FIG. 4A                                    FIG. 4B

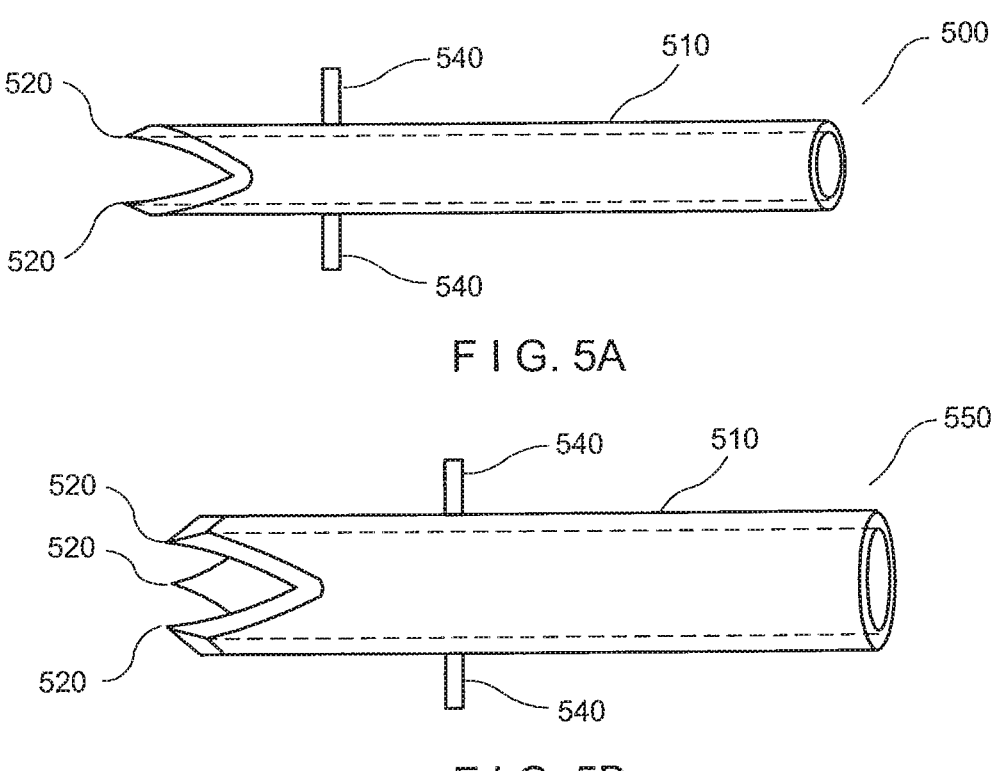
F I G. 5A
F I G. 5B
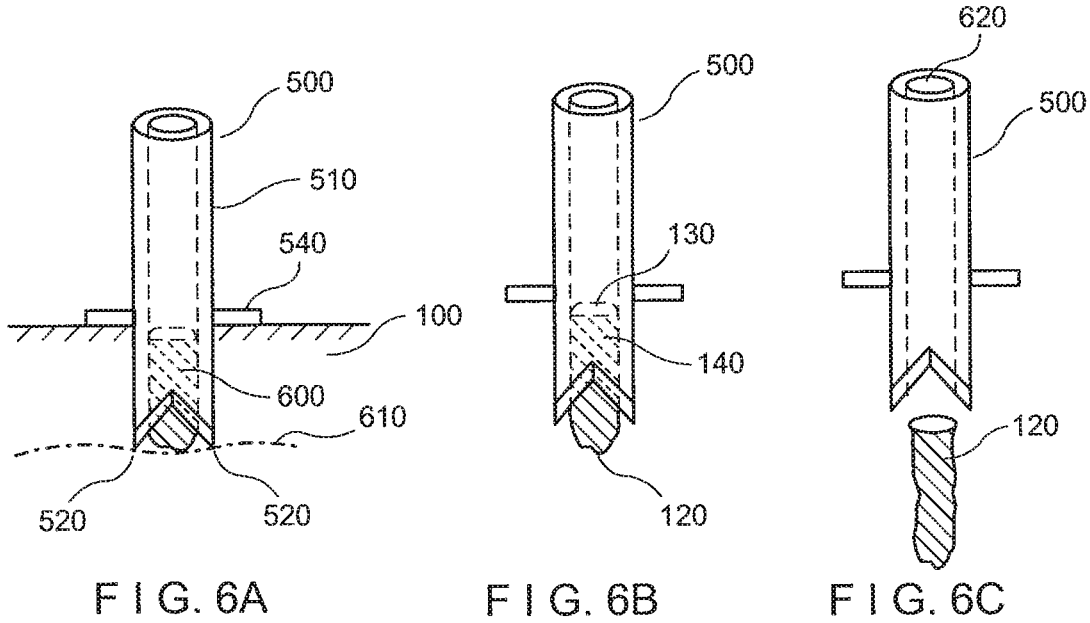
F I G. 6A          F I G. 6B          F I G. 6C

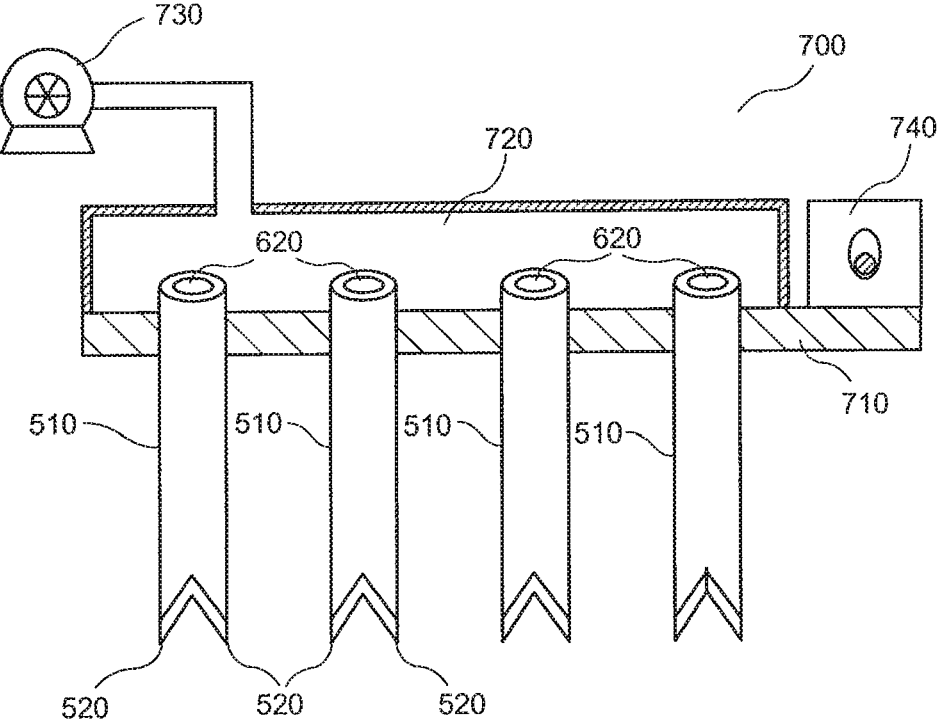
F I G. 7

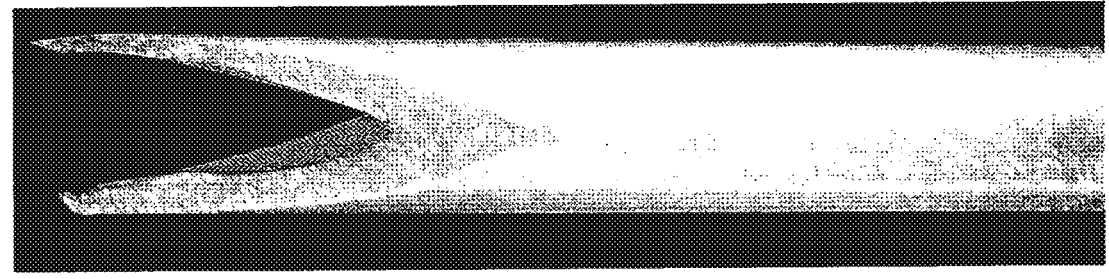
F I G. 8A
F I G. 8B
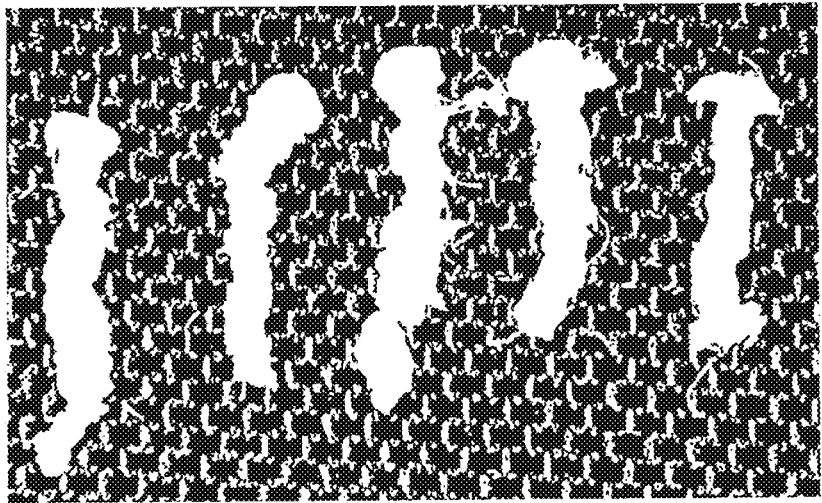
F I G. 9

METHOD AND APPARATUS FOR TISSUE GRAFTING

CROSS-REFERENCE TO RELATED APPLICATION

The present application claims priority from U.S. Provisional Patent Application Ser. No. 61/041,587 filed Apr. 1, 2008, the disclosure of which is incorporated herein by reference in its entirety.

STATEMENT REGARDING FEDERALLY SPONSORED RESEARCH

This invention was made with government support under W911NF-10-1-0017 awarded by the Army Research Laboratory-Army Research Office. The government has certain rights in the invention.

FIELD OF THE INVENTION

The present disclosure relates to exemplary embodiments of method and apparatus for providing tissue grafts using tissue from a donor site.

BACKGROUND INFORMATION

An autograft can refer to tissue transplanted from one part of an individual's body (e.g., a "donor site") to another part (e.g., a "recipient site"). Autografts can be used, for example, to replace missing skin and other tissue and/or to accelerate healing resulting from trauma, wounds, burns, surgery and birth defects. Availability of tissue for autografting can be limited by characteristics of candidate donor sites, including a number and/or total area of tissue grafts, healing behavior of the donor site, similarity of the donor and recipient sites, aesthetic considerations, etc.

Skin grafting can be performed surgically. For example, a conventional autograft procedure may include excision or surgical removal of burn injured tissue, choosing a donor site, which may be an area from which healthy skin is removed to be used as cover for the cleaned burned area, and harvesting, where the graft may be removed from the donor site, e.g., using an instrument similar to an electric shaver. Such instrument (e.g., a dermatome) can be structured to gently shave a piece of tissue, which may be, e.g., about $10/1000$ of an inch thick for a split-thickness graft, from the skin at the unburned donor site to use as a skin graft. The skin graft can then be placed over the cleaned Wound so that it can heal. Donor skin tissue can be removed to such a depth that the donor site can heal on its own, in a process similar to that of healing of a second degree burn.

Two conventional types of autografts which may be used for a permanent wound coverage include sheet grafts and meshed grafts. A sheet graft can refer to a piece of skin tissue removed from an undamaged donor site of the body, in a process that may be referred to as harvesting. The size of the donor skin piece that is used may be about the same size as the damaged area. The sheet graft can be laid over the excised wound, and stapled or otherwise fastened in place. The donor skin tissue used in sheet grafts may not stretch significantly, and a sheet graft can be obtained that is slightly larger than the damaged area to be covered because there may often be a slight shrinkage of the graft tissue after harvesting.

Sheet grafts can provide an improved appearance of the repaired tissue site. For example, sheet grafts may be preferred for use on large areas of the face, neck and hands if they are damaged, so that these more visible parts of the body can appear less scarred after healing. A sheet graft may be used to cover an entire burned or damaged region of skin, e.g., if the damaged site is small. Small areas of a sheet graft can be lost after placement because of a buildup of fluid (e.g., a hematoma) can occur under the sheet graft following placement the sheet graft.

Sheet grafts may be full-thickness or split-thickness. For example, split-thickness skin grafts can be used to cover wounds in burn and skin ulcer patients. A conventional split-thickness graft can be formed, e.g., by harvesting a sheet of epidermis and upper dermal tissue from a donor site, in a procedure similar to that of peeling an apple. The split-thickness graft can then be placed on the location of the burn or ulcer. The skin tissue may then grow back at the donor site following a generally extended healing time. Split-thickness grafts may be preferable to full-thickness grafts because removing large amounts of full-thickness skin tissue from the donor site can lead to scarring and extensive healing times at the donor site, as well as an increased risk of infection. However, skin tissue removed from the donor site for a split-thickness skin autograft can include only a thin epithelial layer, which can lack certain elements of the dermis that improve structural stability and normal appearance in the recipient site.

Full-thickness skin grafts can be formed using sheets of tissue that include the entire epidermis layer and a dermal component of variable thickness. Because the dermal component can be preserved in full-thickness grafts, more of the characteristics of normal skin can, be maintained following the grafting procedure. Full-thickness grafts can contain a greater collagen content, dermal vascular plexus, and epithelial appendages as compared to split-thickness grafts. However, full-thickness grafts can require more precise conditions for survival because of the greater amount of tissue requiring revascularization.

Full-thickness skin grafts can be preferable for repairing, e.g., visible areas of the face that may be inaccessible by local flaps, or for graft procedures where local flaps are contraindicated. Such full-thickness skin grafts can retain more of the characteristics of normal skin including, e.g., color, texture, and thickness, as compared to split-thickness grafts. Full-thickness grafts may also undergo less contraction while healing. These properties can be important on more visible areas such as the face and hands. Additionally, full-thickness grafts in children can be more likely to grow with the individual. However, application of conventional full-thickness skin grafts can be limited to relatively small, uncontaminated, well-vascularized wounds, and thus may not be appropriate for as many types of graft procedures as split-thickness grafts. Additionally, donor sites for full-thickness grafts can require surgical closure or resurfacing with a split-thickness graft.

A meshed skin graft can be used to cover larger areas of open wounds that may be difficult to cover using sheet grafts because of, e.g., a lack of a sufficient area of healthy donor sites. Meshing of a skin graft can facilitate skin tissue from a donor site to be expanded to cover a larger area. It also can facilitate draining of blood and body fluids from under the skin grafts when they are placed on a wound, which my help prevent graft loss. The expansion ratio (e.g., a ratio of the unstretched graft area to the stretched graft area) of a meshed graft may typically be between about 1:1 to 1:4. For example, donor skin can be meshed at a ratio of about 1:1 or 1:2 ratio, whereas larger expansion ratios may lead to a more fragile graft, scarring of the meshed graft as it heals, and/or extended healing times.

A conventional graft meshing procedure can include running the donor skin tissue through a machine that cuts slits through the tissue, which can facilitate the expansion in a pattern similar to that of fish netting or a chain-link fence. Healing can occur as the spaces between the mesh of the stretched graft, which may be referred to as gaps or interstices, fill in with new epithelial skin growth. However, meshed grafts may be less durable graft than sheet grafts, and a large mesh can lead to permanent scarring after the graft heals.

To help the graft heal and become secure, the area of the graft can preferably not be moved for at least about five days following each surgery. During this immobilization period, blood vessels can grow from underlying tissue into the skin graft, and can help to bond the two tissue layers together. About five days after the graft is placed, exercise therapy programs, tub baths, and other normal daily activities can often be resumed. Deep second-degree and full-thickness burns may require skin graft surgery for quick healing and minimal scarring. Large burn sizes can lead to more than one grafting procedure during a hospital stay, and may require long periods of immobilization for healing.

As an alternative to autografting, skin tissue obtained from recently-deceased people (which may be referred to, e.g. as a homograft, an allograft, or cadaver skin) can be used as a temporary cover for a wound area that has been cleaned. Unmeshed cadaver skin can be put over the excised wound and stapled in place. Post-operatively, the cadaver skin may be covered with a dressing. Wound coverage using cadaveric allograft can then be removed prior to permanent autografting.

A xenograft or heterograft can refer to skin taken from one of a variety of animals, for example, a pig. Heterograft skin tissue can also be used for temporary coverage of an excised wound prior to placement of a more permanent autograft, and may be used because of a limited availability and/or high expense of human skin tissue. In some cases religious, financial, or cultural objections to the use of human cadaver skin may also be factors leading to use of a heterograft. Wound coverage using a xenograft or an allograft is generally a temporary procedure which my be used until harvesting and placement of an autograft is feasible.

Epithelial appendages can preferably be regenerated following a grafting procedure. For example, hair can be more likely to grow front full-thickness grafts than from split-thickness grafts, but such hair growth may be undesirable based on the location of the wound. Accordingly, donor sites for full-thickness grafts can be carefully selected based in part, e.g., on patterns of hair growth at the time of surgery. Further, certain hair follicles may not be oriented perpendicular to the skin surface, and they can be transected if an incision provided to remove graft tissue is not oriented properly.

Sweat glands and sebaceous glands located in graft tissue may initially degenerate following grafting. These structures can be more likely to regenerate in full-thickness grafts than in split-thickness grafts because full-thickness grafts can be transferred as entire functional units. For example, sweat gland regeneration can depend in part on reinnervation of the skirt graft with recipient bed sympathetic nerve fibers. Once such ingrowth has occurred, the skin graft can assume the sweating characteristics of the recipient site, rather than retaining the characteristics of the donor site. In contrast, sebaceous gland regeneration may be independent of graft reinnervation and can retain the characteristics of the donor site. Prior to the regeneration, the skin graft tissue may lack normal lubrication of sebum produced by these glands, which can make such grafts more susceptible to injury.

In general, grafting procedures may be limited by the amount of tissue which can be removed from the donor site without causing excessive adverse effects. Full-thickness grafts can provide improved tissue quality at the wound site, but the donor site may be more severely disfigured as described above. Split-thickness grafts can be a compromise between healing times and aesthetic and functional properties of the donor and recipient sites, whereas meshing can provide more extensive graft coverage at the expense of visible scarring.

Harvesting of graft tissue from the donor site generally can generate undesirable large-scale tissue damage to the donor site. On the other hand, small areas of skirt wounding adjacent to healthy tissue can be well-tolerated and my heal quickly. Such healing of small wounds can occur in techniques such as "fractional photothermolysis" or "fractional resurfacing," in which patterns of damage having a small dimension can be created in skin tissue. These exemplary techniques are described, e.g., in U.S. Pat. No. 6,997,923 and U.S. Patent Publication No. 2006/0155266. Small-scale damage patterns can heal quickly by regrowth of healthy tissue, and can further provide desirable effects such as skin tightening without visible scarring.

In view of the shortcomings of the above described procedures for tissue grafting, it may be desirable to provide exemplary embodiments of method and apparatus that can provide tissue suitable for grafting while minimizing unwanted damage to the donor sites.

SUMMARY OF EXEMPLARY EMBODIMENTS

Exemplary embodiments of the present disclosure provide method and apparatus for obtaining small portions of graft tissue that can be accompanied by rapid healing of the donor site. For example, the exemplary embodiment of the method can be provided for obtaining skin graft tissue by harvesting small portions of the tissue, e.g., micrografts, from a donor site.

Such micrografts can comprise skin tissue that can include, e.g., epidermal and dermal tissue, and/or tissue obtained from other body organs. The micrografts can have at least one dimension that is relatively small, e.g., less than about 1 mm, or less than about 0.5 mm, or optionally about 0.3 mm or less, or about 0.2 mm. Such exemplary small dimensions of the micrografts can facilitate both healing of the donor site following harvesting and viability of the micrografts by allowing greater diffusional nourishment of the micrograft tissue. The small regions of damage in the donor site caused by a removal of the tissue portions can heal rapidly with little or no formation of visible scars. The micrografts obtained from skin tissue can include, e.g., epidermal and dermal tissue, and can also include stem cells that can be located proximal to the dermal/fatty layer boundary. The micrografts can also be obtained from other types of tissue, e.g., various internal organs or the like.

A fraction of dermal tissue that is removed from a donor site can be, e.g., less than about 70%, or less than about 50%, although other fractions may be used. The harvested tissue portions can be in the shape of cylinders, elongated strips, or other geometries which can include at least one small dimension. In certain exemplary embodiments, a portion of the tissue at the donor site can be frozen or partially frozen. Such freezing can facilitate cutting, removal and/or viability of the harvested tissue portions.

An exemplary embodiment of the apparatus can be provided for harvesting micrografts that can include a hollow tube. An inner diameter of the hollow tube can be approximately the same size as a diameter or width of the micrograft to be harvested. A distal end of the hollow tube can have two or more points to facilitate separation of the micrografts from the surrounding tissue.

The micrografts can be harvested from the donor site by inserting the exemplary apparatus into tissue at the donor site to a particular depth thereof, and then removing the tube. A stop cart be provided on the tube to control or limit the depth of insertion of the tube. A slight suction or pressure can be provided at a proximal end of the tube to facilitate harvesting of the micrografts and/or their removal from the tube.

A further exemplary embodiment of the apparatus can be provided that includes a plurality of such tubes for simultaneous harvesting of a plurality of micrografts. An enclosure and/or a source of pressure, e.g., a pump or the like, can be provided in communication with the proximal ends of the tubes to facilitate application of pressure and/or suction to the plurality of tubes. A vibrating arrangement can be coupled to the apparatus to facilitate the insertion of the tubes into the donor site.

The exemplary micrografts can be placed in a biocompatible matrix, e.g., to form a graft or directly into tissue at the recipient site The biocompatible matrix can be formed using collagen, polylactic acid, hyaluronic acid, and/or other substances which can support the harvested micrograft tissue portions and promote their growth. The matrix can optionally include, e.g., nutrients and/or other substances to promote tissue growth. The harvested tissue portions can be bonded to the matrix using techniques such as photochemical tissue bonding to provide structural stability. The matrix can then be applied to the recipient site, which can promote growth and revascularization of the tissue portions to form a continuous sheet of the grafted tissue.

The exemplary micrografts can also be gathered in a compact configuration to form graft tissue that can be applied directly to a recipient site. The exemplary micrografts can also be inserted directly into the tissue at a recipient site such as, e.g., scar tissue, using, e.g., the exemplary hollow tubes described herein.

These and other objects, features and advantages of the present disclosure will become apparent upon reading the following detailed description of exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which:

FIG. 1A is a schematic illustration of an exemplary donor site after cylindrical portions of micrograft tissue have been harvested therefrom;

FIG. 1B is a schematic illustration of the exemplary donor site shown in FIG. 1A after healing has occurred;

FIG. 1C is a schematic illustration of an exemplary micrograft that may be removed from the exemplary donor site shown in FIG. 1A;

FIG. 2A is a cross-sectional view of an exemplary graft prepared by providing harvested micrograft tissue portions in a biocompatible matrix;

FIG. 2B is a is a cross-sectional view of the exemplary graft shown in FIG. 2A after it has been placed over a wound and some regrowth has occurred;

FIG. 3A is a schematic illustration of another exemplary donor site after elongated strips of tissue have been harvested therefrom;

FIG. 3B is a schematic illustration of the exemplary donor she shown in FIG. 3A after healing has occurred;

FIG. 3C is a schematic illustration of an exemplary tissue strip that may be removed from the donor site shown in FIG. 3A;

FIG. 4A is a schematic view in plan of a plurality of exemplary cylindrical micrograft tissue portions provided in a compact arrangement to form a graft;

FIG. 4B is a side view of the exemplary micrograft tissue portions shown in FIG. 4A;

FIG. 5A is a schematic illustration of an exemplary apparatus that can be used to harvest micrograft tissue in accordance with first exemplary embodiments of the present disclosure;

FIG. 5B is a schematic illustration of the exemplary apparatus that can be used to harvest the micrograft tissue in accordance with second exemplary embodiments of the present disclosure;

FIG. 6A is a schematic illustration of the exemplary apparatus shown in FIG. 5A that is inserted into an exemplary donor site to harvest an exemplary micrograft;

FIG. 6B is a schematic illustration of the exemplary apparatus shown in FIG. 5A that contains the harvested micrograft;

FIG. 6C is a schematic illustration of the exemplary apparatus shown in FIG. 5A showing the harvested micrograft being removed therefrom;

FIG. 7 is a schematic illustration of the exemplary apparatus that can be used to harvest micrograft tissue in accordance with third exemplary embodiments of the present disclosure;

FIG. 8A is an exemplary image of a distal end of the exemplary apparatus that includes two points;

FIG. 8B is a further exemplary image of the distal end of the exemplary apparatus shown in FIG. 7A; and FIG. 9 is an exemplary image of the micrografts obtained using the exemplary apparatus shown in FIGS. 7-8B.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF EXEMPLARY EMBODIMENTS

Exemplary embodiments of the present disclosure provide methods and apparati for producing autografts, and particularly such methods and apparati which can facilitate more rapid healing of the donor site while providing improved tissue characteristics at the recipient site. Exemplary embodiments of the present disclosure can include a plurality of small-scale tissue portions (e.g., micrografts) that can be used to provide autografts. Such micrografts can avoid significant permanent damage to the donor site while providing graft tissue that can heal rapidly and generate skin tissue having desirable properties at the recipient site.

In exemplary embodiments of the present disclosure, a method can be provided for creating autografts in which tissue portions having at least one small dimension (e.g., micrografts) are harvested from an exemplary donor site 100, as shown in FIG. 1A. The holes 110 shown in FIG. 1A represent regions of the exemplary donor site 100 from which tissue portions (e.g., micrografts) have been removed. These exemplary holes 110 may have art approximately round cross-sectional shape, although other shapes may be used.

The exemplary donor site 100 is shown in FIG. 1B after healing of the harvested tissue has occurred. The small regions of damage 100 created at the donor site by the removed tissue can heal rapidly and/or without visible scarring. For example, the residual pattern of the healed donor site 100 shown in FIG. 1B may not be easily perceptible by the naked eye under normal viewing conditions.

An exemplary micrograft 120 that can be formed, e.g., by harvesting or removing a portion of the tissue from the donor site 100 to form the hole 110 therein, is shown in FIG. 1C. The exemplary micrograft 120 can have an elongated shape that may be approximately cylindrical. The micrografts 120 can include both epidermal tissue 130 and dermal tissue 140 from the exemplary donor site 100. For example, the exemplary micrograft 120 can be about 3 mm in length, which can correspond to a typical total depth of the skin layer (e.g., epidermal and dermal layers). A different length my be used based on the particular skin or tissue characteristics of the donor site 100. In general, it can be preferable to avoid harvesting a significant amount of subcutaneous tissue, so the harvested micrografts 200 can include primarily the epidermal tissue 130 and the dermal tissue 140. A lower portion 150 of the exemplary micrograft 120 can also include stem cells that can be present in a lower portion of the dermal layer of the donor site 100 (e.g., near a dermal/fatty layer boundary).

A width or diameter of the holes 110 produced during harvesting (which can correspond approximately to the diameters of the portions of the harvested micrografts 120) can be less than about 1 mm, or less than about 0.5 mm. In certain exemplary embodiments, the diameter or width can be less than about 0.3 mm, or about 0.2 mm. The size of the exemplary holes 110 can be selected, e.g., based on the effects of creating small damage regions in the donor site 100 which can heal rapidly and/or without scarring, and on creating portions of tissue that may be large enough to form a sufficient amount of graft tissue.

For example, living tissue can be provided with nutrients via a diffusional transport over distances of about 0.1 mm. Accordingly, the exemplary micrografts 120 having at least one dimension that is less than about 0.3 mm or, e.g., about 0.2 mm, can exhibit improved viability and likelihood to survive, and grow when used in a graft. Such exemplary micrografts 120 can be better able to receive nutrients (including, e.g., oxygen) when placed in a recipient site, prior to revascularization of the tissue. Larger micrografts 120 can also benefit from such diffusional transport of nutrients, and can also be more likely to survive than significantly larger portions of graft tissue (e.g., conventional full-thickness, split-thickness or meshed grafts).

A fraction of surface tissue removed from the donor site 100 by harvesting (which can correspond to a fractional surface area of the exemplary donor site 100 occupied by the holes 110) may be less than about 70%, or more preferably less than about 50%. The fraction of tissue removed can be sufficiently large to provide enough harvested micrografts 120 to form a graft therefrom of appropriate size, but small enough to facilitate rapid healing at the donor site 100 based on growth from the remaining undamaged tissue. Other fractions of tissue can be removed from a donor site 100 depending on factors such as, e.g., the particular characteristics of the donor site 100, the size of the graft needed, and the overall amount of donor site tissue available.

In further exemplary embodiments of the present disclosure, a graft 200 can be provided by embedding or inserting a plurality of micrografts 120 in a biocompatible matrix 210 as shown, e.g., in FIG. 2A. The exemplary matrix 210 containing the micrografts 120 can be exposed to nutrients to promote growth of the harvested micrografts 120, e.g., to form a continuous or nearly continuous layer of tissue in the graft 200 after growth has occurred. The exemplary graft 200, which can include the matrix 210 and the micrografts 120, may be placed directly over a recipient site 220 (e.g., a cleaned wound area) as shown in FIG. 2B. The exemplary micrografts 120 can also include stem cells as described herein, which can also facilitate healing and integration of the exemplary micrografts 120 when they are transplanted to the recipient site 220. The recipient site 220 can provide nutrients and/or promote revascularization of the harvested micrografts 120, which can further enhance their growth through the matrix 210 to eventually fill in the spaces separating them. For example, FIG. 2B shows the micrografts 120 after they have begun to grow into the surrounding matrix 210.

In one exemplary embodiment, the micrografts 120 can be placed in the matrix 210 at approximately the same spacing (e.g., a similar areal density) as they were removed from the donor site 100. This exemplary configuration can generate an amount of graft tissue that may be approximately the same size as the overall harvested area of the donor site 100 after the micrografts 120 grow and fill in the spaces between them with new tissue. The average spacing of the micrografts 120 in the matrix 210 can also be increased to form a graft tissue that is larger than the overall area of the harvested donor site 100. The particular spacing of the micrografts 120 in a particular graft 200 can be selected based on factors such as, e.g., the size and fractional damage of the donor site 100, the size of the recipient site 220 to be covered by the skin graft 200, the time needed for the micrografts 120 to regrow and form a continuous tissue layer, the desired appearance of the grafted recipient site, etc. For example, the exemplary micrografts 120 can be spaced far apart in a particular graft, which can provide a larger graft area hut can also require longer healing time and the possibility of some visible scarring or texture in the healed graft 200.

In a further exemplary embodiment, tissue portions 320 such as that shown in FIG. 3C can be harvested in an elongated, narrow strip-like shape. One or more of the exemplary tissue strips 320 can include both epidermal tissue 130 as well as dermal tissue 140, which can be similar to the micrograft 120 shown in FIG. 1C. For example, the height of the exemplary tissue strip 320 may be about 3 mm, or another length that may correspond to a local depth of the dermal layer at the donor site 100. Larger and/or smaller depths can also be selected when harvesting tissue strips 320 based on, e.g., characteristics of the donor and recipient sites, the wound to be repaired by grafting, etc.

Harvesting of such exemplary tissue strips 320 can leave long, narrow grooves 310 in a donor region 100 as shown, e.g., in FIG. 3A. A width of the grooves 310 (and thus a width of the harvested tissue strips 320) can be less than about 1 mm, or less than about 0.5 mm. In certain exemplary embodiments, the width of such tissue strips can be less than about 0.3 mm, or about 0.2 mm. As described herein, such a small dimension can facilitate diffusional transport of nutrients to the graft tissue and can improve viability of the harvested tissue. A depth of the grooves 310 from the skin surface can correspond to the height of the harvested strips 320.

A surface area fraction of the exemplary donor site 310 that is removed to form tissue strips 320 can be less than about 70%, or about 50% or less. Factors governing a selection of parameters associated with the harvested elongated tissue strips 320 (e.g., widths and area fractions removed from the donor site) my be similar to those described above with respect to the substantially cylindrical micrografts 120. The length of the harvested strips 320 can be selected based on factors such as, for example, ease of cutting, removing, and handling the thin tissue strips 320, the size of the donor site 100, etc. The elongated grooves 310 formed in the donor site can may also be able to heal rapidly with little or no visible scarring as shown in FIG. 3B, because of the small lateral dimension and presence of adjacent healthy tissue that can support local tissue regrowth.

The harvested strips 320 can be placed, e.g., in a biocompatible matrix similar to the matrix 210 shown in FIG. 2A. The tissue strips 320 can be arranged in an approximately parallel configuration, e.g., corresponding to the configuration of the donor-site grooves 310 from which they were removed. The spacing between the strips 320 can alternatively be increased or decreased relative to the spacing of the grooves 310 in the donor site 100 as desired, e.g., to provide either larger overall areas of graft tissue or more densely packed graft tissue, respectively. Such harvested tissue strips 320 can be used for certain grafting procedures because the long dimension can preserve structures in the harvested skin tissue that may promote revascularization and improve healing of the graft formed therefrom.

Harvested tissue portions can be removed from the donor site in other shapes, including tile patterns or fractal-like shapes. In general, each removed piece of tissue (and, e.g., each corresponding hole or void in the donor site) can have at least one small dimension that is less than about 1 mm, or less than 0.5 mm. In certain exemplary embodiments, this small dimension can be less than about 0.3 mm, or about 0.2 mm.

In further exemplary embodiments, the harvested tissue portions can be placed at the recipient site in a dense configuration. For example, FIG. 4A is a schematic top view of a plurality of substantially cylindrical micrografts 120 that can be gathered in an exemplary dense arrangement, e.g., where adjacent ones of the exemplary micrografts 120 are in at least partially direct contact each other. FIG. 4B is a schematic side view of the micrografts 120 shown in FIG. 4A. This exemplary dense configuration can provide a graft that is smaller than the overall area of the harvested donor site 100, hut which can tend to heal faster and be less likely to produce visible scarring than grafts formed using spaced-apart harvested tissue portions 120, 320. Similar exemplary dense configurations of harvested tissue can be formed using, e.g., elongated strips of tissue 320 shown in FIG. 3C or the like.

The exemplary biocompatible matrix 210 can be formed using one or more materials structured to provides mechanical stability and/or support to the harvested micrografts 200, and/or which may promote tissue regrowth. Examples of materials which can be used to form the matrix 210 can include polylactic acid (PIA), collagen, or hyaluronic acid (e.g., hyaluranon). Nutrients or other additives can also be provided in the matrix 210 to further promote tissue regrowth. Red or near-infrared light can also be used to illuminate the donor site and/or the recipient site after tissue harvesting and placement of the graft tissue to further promote healing of the tissue.

In certain exemplary embodiments, techniques such as photochemical tissue bonding can be used to improve mechanical stability of the micrografts 120 and/or tissue strips 320 in the matrix 210. For example, a technique for photochemical tissue bonding is described in U.S. Pat. No. 7,073,514). This technique includes an application of a photosensitizer to a tissue, followed by irradiation with electromagnetic energy to produce a tissue seal. For example, a photosensitizer such as Rose Bengal can be applied to the matrix 210 containing the exemplary micrografts 120 and/or tissue strips 320, followed by exposure of the matrix to green light for about two minutes. Photochemical tissue bonding can catalyze a polymerization reaction which may facilitate a stronger bonding of the micrografts 120 and/or tissue strips 320 to the matrix 210, where the matrix 210 can include a protein such as, e.g., hyaluronic acid or collagen.

In further exemplary embodiments of the present disclosure, an apparatus 500 can be provided, such as that shown in FIG. 5A, which can facilitate harvesting of the exemplary micrografts 120 from the donor site 100 as described herein. The exemplary apparatus 500 can include a hollow tube 510 that can be formed of metal or another structurally rigid material. For example, the tube 510 can be formed using a stainless steel, a biopsy needle, or a similar structure. The tube 510 can be coated with a lubricant or low-friction material, such as Teflon®, to further facilitate the passage of the tubes 510 through the donor site tissue 100.

The inner diameter of the tube 510 can be selected to approximately correspond to a particular diameter of a micrograft 120 to be removed from the donor site 100 as described herein. For example, 18 or 20 gauge biopsy needles (e.g., having an inner diameter of 0.838 mm and 0.564 mm, respectively) or the like can be used to form the tube. A biopsy tube having a larger gauge (and smaller inner diameter) can also be used. A width or diameter of the harvested micrograft 120 can be slightly smaller than the inside diameter of the apparatus 500 used to harvest it.

A distal end of the tube 510 can be shaped to form a plurality of points 520. For example, the two exemplary points or extensions 520 shown in FIG. 5A can be formed by grinding opposite sides of the tube 510 at an angle relative to the long axis of the tube 510. In a further exemplary embodiment as shown in FIG. 5B, an exemplary apparatus 550 can be provided that includes a tube 510 with three points or extensions 520 provided at a distal end thereof. This exemplary configuration can be formed, e.g., by grinding 3 portions of the tube 519 at an angle relative to the long axis thereof, where the three portions can be spaced apart by about 120 degrees around the perimeter of the tube 510. In still further exemplary embodiments, an apparatus can be provided for harvesting micrografts that includes a tube having more than three points or extensions 520 provided at a distal end thereof, e.g., a tube 510 having four, five, six, seven or eight points 520.

The exemplary points or extensions 520 can facilitate insertion of the apparatus 500, 550 into tissue at the donor site 100. The exemplary points or extensions 520 that are formed, e.g., by grinding portions of the distal end of the tube 510 can also have a beveled edge along their sides, which can further facilitate insertion of the apparatus 500, 550 into donor-site tissue.

The exemplary apparatus 500 can also included a collar or stop 540 provided on an outer surface of the tube 510. The exemplary stop 540 can be affixed to the tube 510 at a particular distance from the ends of the tips 520, or this distance may be adjustable, e.g., over a range of lengths by moving the stop 540 along the axis of the tube 510.

FIG. 6A illustrates the exemplary apparatus 500 after it is inserted into the tissue at the donor situ 100, e.g., until the stop 540 contacts the surface of the donor site 100. A portion of tissue 600 can be present within a lower portion of the tube 510. Lateral sides of this tissue portion 600 can be cut or severed from the surrounding tissue by the distal end of the tube 510 and/or points 520 as the tube 510 penetrates into the donor site tissue 100. Such tissue 600 can remain within the tube 510, and be separated from the donor site 100 to form the micrograft 120, e.g., when the tube 510 is removed from the donor site 100 as shown in FIG. 6B. The exemplary micrograft 120 thus formed can include both epidermal tissue 130 and dermal tissue 140.

The exemplary micrograft 120 can be removed from the apparatus, e.g., by providing pressure through an opening 620 at a proximal end of the tube 510 as shown, e.g., in FIG. 6C. Such pressure can be provided, e.g., by blowing into the opening, by squeezing a flexible bulb attached thereto, by opening a valve leading from a source of elevated pressure such as a small pump, etc. Alternatively, the exemplary micrografts 120 can be harvested by insetting the exemplary apparatus 500 into a plurality of locations of the donor site 100. Each micrograft 120 within the tube 510 can then push any micrografts above it towards the opening 620. Once the tube 520 has been filled with the harvested tissue, each additional insertion of the exemplary apparatus 500 into the donor site 100 can facilitate pushing of an uppermost micrograft 120 within the tube 510 out of the proximal opening 620.

The exemplary apparatus 500 can be inserted into the donor site tissue 100 to a depth corresponding approximately to a desired length of the harvested micrografts 120. Such distance can be determined and/or controlled, e.g., by appropriate placement or adjustment of the stop 540 on the exemplary apparatus 500. For example, the exemplary apparatus 500 can be configured or structured such that the points or extensions 520 extend to a location at or proximal to the dermal/fatty layer junction 610 as shown in FIG. 6A. For example, the micrograft 120 can be removed from the donor site 100 by removing the apparatus 500 from the donor site without rotating the tube 510 around the axis thereof. In contrast, conventional biopsy needles and the like may require a rotation around the long axis to facilitate removal of tissue samples from the surrounding tissue. The points or extensions 520 provided on the exemplary apparatus 500 can facilitate such removal of the micrograft 120 from the surrounding tissue at the donor site 100.

In certain exemplary embodiments, some or all of the tissue at the donor site can be cooled, frozen, or partially frozen prior to harvesting the micrografts 120. Such freezing can facilitate cutting, removal, handling, and/or viability of the micrografts 120. The donor site tissue 100 can be cooled or frozen using conventional cooling techniques such as, e.g., applying a crypspray or contacting a surface of the donor site 100 with a cooled object for an appropriate duration. The exemplary apparatus 500 can also be cooled prior to harvesting the micrografts 120. Such cooling and/or freezing can, e.g., increase a mechanical stability of the micrografts 120 when they are harvested and/or placed in the matrix 210.

The exemplary micrografts 120 can be provided into the matrix 210 using various techniques. For example, the individual micrografts 120 can be inserted into particular locations of the matrix 210 using, e.g., tweezers or the like. The exemplary apparatus 500 containing a harvested micrograft 120, as shown in FIG. 6B, can also be inserted into a location of the matrix 210, and pressure can be applied to the proximal opening 620 to push the micrograft 120 into the matrix 210. The exemplary apparatus 500 can then be removed from the matrix 210, and the procedure repeated to place a plurality of micrografts 120 in the matrix 210. The proximal opening 620 can be covered while the apparatus 500 is being inserted into the matrix 210 to prevent the micrograft 120 from being pushed further up into the apparatus 500. For example, the upper portion of the tube 510 can be filled with a fluid, e.g., water or a saline solution, to provide an incompressible volume that can further prevent the micrograft 120 from rising further up into the tube 510. Such fluid can also facilitate a removal of the micrograft 120 from the exemplary apparatus 500 by providing pressure at the proximal opening 620.

Exemplary procedures for harvesting and implanting the micrografts 120 described herein can be used to provide the micrografts 120 directly into, e.g., substantially whole tissue at the recipient site. For example, the micrografts 120 can be harvested from the donor site 100 that can contain melanocytes, and inserted directly into tissue at a recipient site that lacks sufficient melanocytes. Such exemplary procedure can be used to recipient skin tissue, e.g., to treat vitiligo or similar conditions. Tissue at the recipient site can also be frozen or partially frozen, as described herein, prior to the insertion of the micrografts 120 therein.

The exemplary micrografts 120 can also be harvested from a healthy donor site and placed directly into scar tissue to facilitate growth of healthy tissue in the scar. Optionally, portions of tissue can be removed from the recipient site prior to placing micrografts in holes at the recipient site that are formed by the removal of these tissue portions. The holes can be about the same size or slightly larger than the size of the micrografts 120 to be inserted therein, to facilitate such insertion. The holes can be formed at the recipient site, e.g., using one or more of the tubes 510 as described herein, by removing or ablating the tissue using, e.g., an ablative laser, etc.

In a further exemplary embodiment of the present disclosure, an exemplary apparatus 700 can be provided as shown in FIG. 7. The apparatus 700 can include, e.g., a plurality of tubes 510 affixed or mechanically coupled to a base 710. The tubes 510 can be provided in various configurations, e.g., in a linear array, or in any one of various two-dimensional patterns along the base 710. The number of tubes 510 provided in the exemplary apparatus 700 can be, for example, greater than five tubes 510, more than about 10 tubes, or more than about 30 tubes 510.

An enclosure 720 may be provided in communication with proximal openings 620 of the tubes 510. The enclosure 720 can also be provided in communication, e.g., with a pressure source 730. For example, the pressure source 730 can include a pump or a deformable bulb or the like. The pressure source 730 can include, e.g., a flexible membrane provided in communication with the enclosure 720, such that an elevated pressure can be provided within the enclosure 720 when the membrane is deformed. Such configurations can facilitate applying pressure to the proximal openings 620 for removal and/or insertion of the micrografts 120 that can be harvested in the tubes 510, as described herein.

A vibrating arrangement 740 may optionally be provided in the apparatus 700. The vibrating arrangement 740 can be mechanically coupled to the base 710 and/or the tubes 510 to facilitate the insertion of the tubes 510 into the tissue or matrix material for harvesting or placement of micrografts 120. The vibrating arrangement 740 can have an amplitude of vibration in the range of about 50-500 µm, or between about 100-200 µm. The frequency of the induced vibrations can be between about 10 Hz and about 10 kHz, or between about 500 Hz and about 2 kHz, or even about 1 kHz. Particular vibration parameters can be selected based on, e.g., the size, average spacing, and material of the tubes 510, the number of tubes 510 in the exemplary apparatus 700, and/or the tissue being treated. The vibrating arrangement 740 can include circuitry configured to adjust the amplitude and/or frequency of the vibrations.

The exemplary apparatus 700 can be used to simultaneously obtain a plurality of the micrografts 120 in the plurality of the tubes 510. Exemplary procedures for obtaining and removing such micrografts 120 using the exemplary apparatus 700 can be similar to the procedures described herein for obtaining single micrografts 120 using the exemplary apparatus 500 shown in FIGS. 6A-6C.

The vibration can also assist in severing tissue proximal to the distal end of the tubes 510 after they are fully inserted into the donor site 100. This can facilitate separation and/or extraction of the tissue portions within the tubes 510 from the donor site 100. These tissue portions can also be held by friction within the tubes 510 as the tubes 510 are withdrawn from the donor site 100.

In further embodiments, the donor site tissue can be pre-cooled prior to insertion of the tubes 510, e.g., using convective or conductive techniques such as applying a cryospray or contacting the tissue surface with a cooled object. Cooling of the donor site 100 can reduce a sensation of pain when the tubes 510 are inserted into the donor site tissue 100, and can also make the tissue 100 more rigid and facilitate a more accurate severing of tissue portions (e.g., micrografts 120) by the tubes 510.

The positions and spacing of the tubes 510 in the exemplary apparatus 700 can be determined, e.g., based on characteristics of the micrografts 120 to be obtained, a damage pattern to the donor site 100, and/or other factors as described herein above. The number of the tubes 510 provided in the exemplary apparatus 700 can be selected based on various factors. For example, a larger number of tubes 510 may be desirable to allow more micrografts 120 to be harvested simultaneously from a donor site 100. Such exemplary configuration can facilitate a more efficient harvesting process. A smaller number of the tubes 510 can be easier to insert simultaneously into the donor site tissue 100. Further, the exemplary apparatus 500 having a very large number of the tubes 510 can be difficult to manufacture and/or maintain.

The harvested tissue portions can be deposited directly from the tubes 510 into the biocompatible matrix material 210. The tubes 510 and tissue portions contained therein can be cooled before removal of the tissue portions. This can stiffen the tissue portions within the tubes 510 and make them easier to manipulate and position.

In a further embodiment, an apparatus can be provided that includes a plurality of substantially parallel blades. The ends of certain ones of the adjacent blades can be connected or closed off to provide, e.g., narrow rectangular openings between adjacent blades. Such an exemplary apparatus can be used, e.g., to form the tissue strips 320 such as that shown in FIG. 3C. Spacings, lengths, and other features of this exemplary apparatus can be selected based on factors similar to those described herein, e.g., for the exemplary apparati 500, 700.

In further exemplary embodiments of the present disclosure, the exemplary methods and apparati described herein can be applied to other tissues besides skin tissue, e.g., internal organs such a s a liver or heart, and the like. Thus, grafts can be formed for a variety of tissues while producing little damage to a donor site and facilitating rapid healing thereof, while creating graft tissue suitable for placement at recipient sites.

EXAMPLE

An image of a distal end of an exemplary apparatus that includes two points is shown in FIG. 8A. This apparatus is similar to the exemplary apparatus 500 illustrated, e.g., in FIG. 5A. A further rotated image of this exemplary apparatus is shown in FIG. 8B. The exemplary apparatus was formed using a tube having an outside diameter of about 1 mm, and an inside diameter of about 0.5 mm. The points or extensions were formed by grinding two opposite sides of the distal end of the tube at an appropriate angle relative to the axis of the tube. The angle used was about 30 degrees, although other angles may also be used. A beveled edge of the tube wall can be seen along the sides of the points or extensions. The shape of these points can facilitate insertion of the apparatus into tissue of a donor site and/or separation of a portion of micrograft tissue from the donor site, as described in more detail herein. For example, such micrografts can be separated and removed from the donor site by inserting and withdrawing the apparatus from the donor site tissue without rotating the tube along its axis.

FIG. 9 is an image of a plurality of micrografts obtained from a donor site of ex vivo skin tissue using the apparatus shown in FIGS. 8A-8B. The micrografts are elongated and substantially similar in shape, although details of the shapes my be somewhat irregular. An upper portion of these micrografts includes epidermal tissue, and the lower portion of these micrografts include dermal tissue removed from the donor site. The width of these micrografts is slightly smaller than the internal diameter of the tube shown in FIGS. 5A-8B that was used to harvest them.

The micrografts shown in FIG. 9 were removed from the apparatus by inserting the exemplary apparatus into donor site a plurality of times, until the tube was filled with harvested tissue. Each subsequent insertion of the apparatus into the donor site tissue then forced the uppermost micrograft out of the proximal end of the tube, where it was retrieved individually for analysis. Such micrografts can also be removed by applying pressure to the proximal end of the tube containing the micrograft, to force it out of the distal end of the tube as described herein.

The foregoing merely illustrates the principles of the present disclosure. Various modifications and alterations to the described embodiments will be apparent to those skilled in the art in view of the teachings herein. It will thus be appreciated that those skilled in the art will be able to devise numerous techniques which, although not explicitly described herein, embody the principles of the present disclosure and are thus within the spirit and scope of the present disclosure. All patents and publications cited herein are incorporated herein by reference in their entireties.

15

What is claimed is:

1. An apparatus comprising:
a plurality of hollow tubes, each of the plurality of hollow
tubes comprising:
a first exterior side and a second exterior side opposite
the first exterior side;
only two extensions disposed at a distal end thereof;
a first bevel on the first exterior side at the distal end,
the first bevel being disposed between the two exten-
sions;
a second bevel on the second exterior side at the distal
end, the second bevel being disposed between the
two extensions, wherein the two extensions, the first
bevel, and the second bevel are configured to sever
a corresponding skin micrograft upon insertion of the
respective hollow tube into a donor site; and
an inner diameter of 1 millimeter or less configured to
retain the skin micrograft upon withdrawal of the
respective hollow tube from the donor site;
a base configured to secure the plurality of hollow tubes,
such that the distal ends of the plurality of hollow tubes
are aligned during insertion into the donor site;
wherein each skin micrograft retained by the respective
hollow tube is separatable from the donor site without
rotating the respective hollow tube around an axis
thereof; and
wherein the plurality of hollow tubes includes at least one
of:
at least four hollow tubes;
more than five hollow tubes;
more than 10 hollow tubes; or
more than 30 hollow tubes.

2. The apparatus of claim 1, wherein the inner diameter of
each hollow tube of the plurality of hollow tubes is about 0.5
millimeters or less.

3. The apparatus of claim 1, further comprising a vibrating
arrangement in contact with the base, the vibrating arrange-
ment being configured to vibrate the plurality of hollow
tubes to facilitate the insertion into the epidermis.

4. The apparatus of claim 1, wherein, for each hollow tube
of the plurality of hollow tubes, a contact friction between
the skin micrograft and the hollow tube retains the skin
micrograft within the hollow tube upon withdrawal from the
donor site.

5. The apparatus of claim 1, wherein each hollow tube of
the plurality of hollow tubes has a circular cross-section; and
wherein each hollow tube of the plurality of hollow tubes
is configured to retain the respective skin micrograft
having a cylindrical shape.

6. The apparatus of claim 1, further comprising a stop
connected to the plurality of hollow tubes and disposed at a
fixed distance from the distal ends of the plurality of hollow
tubes; and at least one of:
the fixed distance from the distal ends is configured to
correspond to an approximate stem cell depth of the
donor site; or
the fixed distance from the distal ends corresponds to a
skin micrograft including at least one melanocyte.

7. The apparatus of claim 1, wherein the plurality of
hollow tubes are a fixed distance from one another, such that
the captured skin micrografts comprise less than 50% of the
donor site.

8. The apparatus of claim 1, wherein each extension of the
only two extensions is angled thirty degrees relative to a
center axis of the respective hollow tube.

9. The apparatus of claim 1, wherein the plurality of
hollow tubes are aligned and affixed to the base such that the
skin micrografts are individually retained within the plural-
ity of hollow tubes.

10. An apparatus comprising:
a plurality of hollow tubes, each of the plurality of hollow
tubes comprising:
a first exterior side and a second exterior side opposite
the first exterior side;
only two extensions disposed at a distal end thereof;
a first bevel on the first exterior side at the distal end,
the first bevel being disposed between the two exten-
sions;
a second bevel on the second exterior side at the distal
end, the second bevel being disposed between the
two extensions, wherein the two extensions, the first
bevel, and the second bevel are configured to sever
a corresponding skin micrograft upon insertion of the
respective hollow tube into a donor site; and
an inner diameter of 1 millimeter or less configured to
retain the skin micrograft upon withdrawal of the
respective hollow tube from the donor site;
a base configured to secure the plurality of hollow tubes,
such that the distal ends of the plurality of hollow tubes
are aligned during insertion into the donor site;
wherein each skin micrograft retained by the respective
hollow tube is separatable from the donor site without
rotating the respective hollow tube around an axis
thereof; and
wherein the plurality of hollow tubes form a linear array
of hollow tubes.

11. The apparatus of claim 10, wherein the inner diameter
of each hollow tube of the plurality of hollow tubes is about
0.5 millimeters or less.

12. The apparatus of claim 10, further comprising a
vibrating arrangement in contact with the base, the vibrating
arrangement being configured to vibrate the plurality of
hollow tubes to facilitate the insertion into the epidermis;
and
wherein the vibrating arrangement is configured to vibrate
after insertion of the plurality of hollow tubes to ensure
severance of the skin micrografts.

13. The apparatus of claim 10, wherein, for each hollow
tube of the plurality of hollow tubes, a contact friction
between the skin micrograft and the hollow tube retains the
skin micrograft within the hollow tube upon withdrawal
from the donor site.

14. The apparatus of claim 10, wherein each hollow tube
of the plurality of hollow tubes has a circular cross-section;
and
wherein each hollow tube of the plurality of hollow tubes
is configured to retain the respective skin micrograft
having a cylindrical shape.

15. The apparatus of claim 10, further comprising a stop
connected to the plurality of hollow tubes and disposed at a
fixed distance from the distal ends of the plurality of hollow
tubes; and at least one of:
the fixed distance from the distal ends is configured to
correspond to an approximate stem cell depth of the
donor site; or
the fixed distance from the distal ends corresponds to a
skin micrograft including at least one melanocyte.

16. The apparatus of claim 10, wherein the plurality of
hollow tubes are a fixed distance from one another, such that
the captured skin micrografts comprise less than 50% of the
donor site.

17. The apparatus of claim 10, wherein each extension of the only two extensions is angled thirty degrees relative to a center axis of the respective hollow tube.

18. The apparatus of claim 10, wherein the plurality of hollow tubes are aligned and affixed to the base such that the skin micrografts are individually retained within the plurality of hollow tubes.

19. An apparatus comprising:

a plurality of hollow tubes, each of the plurality of hollow tubes comprising:

a first exterior side and a second exterior side opposite the first exterior side;

only two extensions disposed at a distal end thereof;

a first bevel on the first exterior side at the distal end, the first bevel being disposed between the two extensions;

a second bevel on the second exterior side at the distal end, the second bevel being disposed between the two extensions, wherein the two extensions, the first bevel, and the second bevel are configured to sever a corresponding skin micrograft upon insertion of the respective hollow tube into a donor site; and an inner diameter of 1 millimeter or less configured to retain the skin micrograft upon withdrawal of the respective hollow tube from the donor site;

a base configured to secure the plurality of hollow tubes, such that the distal ends of the plurality of hollow tubes are aligned during insertion into the donor site;

wherein each skin micrograft retained by the respective hollow tube is separatable from the donor site without rotating the respective hollow tube around an axis thereof;

wherein the plurality of hollow tubes form a linear array of hollow tubes; and wherein the plurality of hollow tubes includes at least one of:

at least four hollow tubes;

more than five hollow tubes;

more than 10 hollow tubes; or more than 30 hollow tubes.

20. The apparatus of claim 19, wherein the inner diameter of each hollow tube of the plurality of hollow tubes is about 0.5 millimeters or less.

\* \* \* \* \*